United States Patent
Miyatani et al.

(10) Patent No.: US 7,866,464 B2
(45) Date of Patent: Jan. 11, 2011

(54) THIN-SECTION CONVEYOR APPARATUS, THIN-SECTION SCOOPING TOOL, AND METHOD FOR TRANSPORTING THIN SECTIONS

(75) Inventors: Tatsuya Miyatani, Chiba (JP); Koji Fujimoto, Chiba (JP); Tetsumasa Ito, Chiba (JP)

(73) Assignee: Seiko Instruments Inc. (JP)

( * ) Notice: Subject to any disclaimer, the term of this patent is extended or adjusted under 35 U.S.C. 154(b) by 696 days.

(21) Appl. No.: 11/829,555

(22) Filed: Jul. 27, 2007

(65) Prior Publication Data

US 2008/0044260 A1      Feb. 21, 2008

(30) Foreign Application Priority Data

| Jul. 28, 2006 | (JP) | ............................. 2006-206427 |
| May 14, 2007 | (JP) | ............................. 2007-127858 |

(51) Int. Cl.
   *B65G 15/30*   (2006.01)
   *G01N 1/06*    (2006.01)
   *G01N 35/04*   (2006.01)

(52) U.S. Cl. .................... 198/844.1; 198/846; 198/847; 436/518

(58) Field of Classification Search ............. 198/844.1, 198/846, 847; 436/518
   See application file for complete search history.

(56) References Cited

U.S. PATENT DOCUMENTS

| 4,071,315 | A |   | 1/1978 | Chateau |
| 5,119,938 | A | * | 6/1992 | Beckh et al. ................. 198/847 |
| 5,495,935 | A | * | 3/1996 | Zabron et al. ................ 198/847 |
| 5,772,848 | A | * | 6/1998 | Dutt ........................ 162/358.4 |
| 5,792,323 | A | * | 8/1998 | Grondahl .................. 162/358.4 |
| 5,906,269 | A | * | 5/1999 | Zabron et al. ................ 198/847 |
| 6,173,831 | B1 | * | 1/2001 | Grabscheid et al. ...... 198/844.1 |
| 6,428,874 | B1 | * | 8/2002 | McGahern et al. .......... 428/167 |
| 6,769,535 | B2 | * | 8/2004 | Zilker et al. ................. 198/847 |

(Continued)

FOREIGN PATENT DOCUMENTS

DE          43 07 738 A1     9/1993

(Continued)

OTHER PUBLICATIONS

Partial European Search Report issued Jul. 28, 2008 in European patent application No. 07252961.3.

(Continued)

*Primary Examiner*—Mark A Deuble
(74) *Attorney, Agent, or Firm*—Brinks Hofer Gilson & Lione

(57) ABSTRACT

A thin-section conveyor apparatus for transporting thin sections that have been prepared by thinly cutting an embedded block, which transports the thin sections to a liquid bath by mounting them on the upper plane of a conveyor belt having a longitudinal linear body extended along the direction of transportation and a transverse linear body disposed perpendicular to the longitudinal linear body, provided that the density of the transverse linear body for the part on which the thin sections are to be mounted is lower than that of the transverse linear body of the other places. It provides thin sections almost free of entraining bubbles. A thin-section scooping tool and a method for transporting thin sections are also proposed.

6 Claims, 11 Drawing Sheets

U.S. PATENT DOCUMENTS

2005/0211533 A1 * 9/2005 Ishino et al. ................ 198/846
2006/0008790 A1   1/2006 Hayworth et al.

FOREIGN PATENT DOCUMENTS

| | | |
|---|---|---|
| EP | 0 088 549 A1 | 9/1983 |
| EP | 0 261 667 A2 | 3/1988 |
| EP | 1 498 718 A1 | 1/2005 |
| EP | 1 826 546 A2 | 8/2007 |
| FR | 2 542 870 A1 | 9/1984 |
| JP | 05-273094 | 10/1993 |
| JP | 6-323967 A | 11/1994 |
| JP | 9-21733 A | 1/1997 |
| JP | 2005-174657 A | 6/2005 |
| WO | WO 2004/112571 A2 | 12/2004 |

OTHER PUBLICATIONS

Extended European Search Report issued Oct. 8, 2008 in European patent application No. 07252961.3, 15 pages.

* cited by examiner ial application claims priority under 35 U.S.C. §119 to Japanese Patent Application Nos. JP2006-206427 filed Jul. 28, 2006, and JP2007-127858 filed May 14, 2007, the entire content of which is hereby incorporated by reference.

THIN-SECTION CONVEYOR APPARATUS, THIN-SECTION SCOOPING TOOL, AND METHOD FOR TRANSPORTING THIN SECTIONS

This application claims priority under 35 U.S.C. §119 to Japanese Patent Application Nos. JP2006-206427 filed Jul. 28, 2006, and JP2007-127858 filed May 14, 2007, the entire content of which is hereby incorporated by reference.

BACKGROUND OF THE INVENTION

1. Field of the Invention

The present invention relates to a thin-section conveyor apparatus for transporting thin sections obtained by thinly cutting embedded blocks having embedded therein the biological samples taken out from human bodies, laboratory animals, and the like, as well as to a thin-section scooping tool for scooping thin sections that are floating on the liquid surface in a bath, and to a method for transporting thin sections utilizing the thin-section conveyor apparatus.

2. Description of the Related Arts

As a method for testing and observing biological samples taken from human bodies or laboratory animals and the like, conventionally known is a method which comprises preparing an embedded block by embedding biological samples in an embedding medium, thinly cutting the thus prepared embedded blocks into extremely thin sections several micrometers in thickness, and then melting the embedding medium to observe the sample. In this method, the thin sections are prepared by fixing the embedded block on a specimen stage, and then moving a cutter at a predetermined speed to cut out thin sections about 3 to 5 μm in thickness. The thin sections thus prepared are then hooked with fine threads and the like to feed them to the next process steps such as the flattening step and the baking step.

Conventionally, the process step for taking out and sending the thus prepared thin sections to the next process has been carried out manually because the thin sections were extremely thin and were apt to suffer damages such as curls, wrinkles, breaks, and the like. On the other hand, in preclinical tests, for instance, several hundreds of embedded blocks are prepared per test, and several thin sections are prepared from a single embedded block. This requires the operator to prepare a huge number of thin sections and send them to the next process step. Accordingly, attempts have been made to automate these process steps.

Under such circumstances, for instance, there is proposed an apparatus which comprises moving an embedded block by clamping it with a clamping mechanism, preparing thin sections by thinly cutting out the embedded block using a fixed cutter, and transferring the thus prepared thin sections by using a belt and floating them in a water bath, thereby extending the thin sections (see, for example, JP-A-H05-273094).

However, according to the technology disclosed in JP-A-H05-273094, bubbles may be entrained between the thin section and the surface of the water when the thin sections transported by the belt are set afloat on the surface of the water. Then, the thin sections are mounted on a glass slide, and finally, they are tightly adhered to the glass slide after they are subjected to a hot-plate flattening step and a drying step. However, if bubbles should be entrained between the glass slide and the thin section, the adhesiveness of the thin sections to the glass slide decreases to cause the problem of peeling off in the subsequent dyeing step. Otherwise, even if the thin section stay adhered without peeling off, the bubble-entrained part appears as a part differing in color density which is detrimental in microscopic observations.

Accordingly, this invention has been accomplished based in the light of the aforementioned circumstances, and the invention provides a thin-section conveyor apparatus, a thin-section scooping tool, and a method for transporting thin sections, which are almost free of entraining bubbles, or, even if the bubbles should be entrained, which can rapidly remove the bubbles when the thin section are floated on the surface of a liquid.

SUMMARY OF THE INVENTION

In order to solve the aforementioned problems, this invention proposes the following solutions.

The thin-section conveyor apparatus according to the invention is a thin-section conveyor apparatus for transporting thin sections that have been prepared by thinly cutting an embedded block, which transports the thin sections to a liquid bath by mounting them on the upper plane of a conveyor belt having a longitudinal linear body extended along the direction of transportation and a transverse linear body disposed perpendicular to the longitudinal linear body, and is characterized in that the density of the transverse linear body at the part on which the thin sections are to be mounted is lower than that of the transverse linear body of the other places.

The term "disposed perpendicular to" signifies not only the cases in which the linear bodies make precisely a right angle, but also those cases in which the linear bodies are somewhat displaced when they are woven to make angles near to a right angle.

The "linear body" as referred herein encompasses a broad range of linear shaped bodies, such as those woven into threads, those obtained by cutting films into linear shapes, resin monofilaments such as fishing lines, which are spun out from an intruder, and metallic monofilaments.

In accordance with the thin-section conveyor apparatus above, in the case the thin sections are transported to the liquid bath using the conveyor belt, the linear body extended along the direction of transportation of the conveyor belt gradually intrudes into the liquid from the front end. Accordingly, the linear body is fundamentally free of entraining air because it is sequentially soaked or get acquainted with water. In contrast to this, the linear body in the transverse direction, which is perpendicular to the transportation direction of the conveyor belt, is wholly immersed in the liquid of the liquid bath at the one time. Accordingly, the linear body in the transverse direction has very short time to get soaked or acquainted with the liquid, and these results in easy entrainment of air. In addition, the presence of a linear body in the transverse direction causes irregularities to generate in longitudinal linear body or transverse linear body itself at the part the transverse linear body crosses the perpendicular linear body; these irregularities easily entrain air.

At the parts of the conveyor belt in which thin sections are mounted, the density of the transverse linear body is set lower as compared with the density of the transverse linear body of the other parts. That is, by decreasing the number of the transverse linear body that is apt to entrain air at the moment it is immersed into the liquid, the air entraining ratio can be lowered, and thereby the fear of entraining air under the thin section can be reduced.

Furthermore, the thin-section conveyor apparatus according to the invention is a thin-section conveyor apparatus for transporting thin sections that have been prepared by thinly cutting an embedded block, which transports the thin sections to a liquid bath by mounting them on the upper plane of a conveyor belt, wherein the part of the conveyor belt on which the thin sections are to be mounted is made only of plural linear bodies extended along the direction of transportation of the conveyor belt.

In accordance with the above thin-section conveyor apparatus, the part of the conveyor belt on which the thin sections are mounted is made of only plural linear body extended along the direction of transportation of the conveyor belt, and is free of linear bodies extended along the direction perpendicular to the plural linear bodies. Thus, the possibilities of entraining air under the thin sections are further reduced.

Further, the thin-section conveyor apparatus according to the invention is a thin-section conveyor apparatus for transporting thin sections that have been prepared by thinly cutting an embedded block, which transports the thin sections to a liquid bath by mounting them on the upper plane of a conveyor belt, wherein the conveyor belt is provided as such that a single linear body is extended along the direction of transportation and wound spirally around a starting point roller and an ending point roller in such a manner that the linear body may be disposed in parallel to and spaced out from each other.

The term "in parallel" is used not only in the narrower definition of making an angle of 180° with respect to each other, but also in the case the linear bodies are disposed spaced out from each other by making an angle slightly larger or smaller than 180°, for instance, by making an angle in a range of from 170° to 190°.

In accordance with the above thin-section conveyor apparatus, the conveyor belt comprises longitudinal linear bodies alone and free from transverse linear bodies. Thus, as stated earlier, the possibilities of entraining air under the thin sections is further reduced.

In addition, since the conveyor belt is basically formed by spirally winding a single linear body, the linear bodies between the starting point roller and an ending point roller are connected to each other. Thus, the tensile strength adjustment is unnecessary because it can be automatically equalized.

Furthermore, the thin-section conveyor apparatus according to the invention comprises linear bodies that are hydrophilic.

According to the thin-section conveyor apparatus above, the linear bodies are rendered hydrophilic. Thus, in the case the thin sections are mounted on the linear bodies and transported to the liquid bath to set them afloat, the linear bodies become better acquainted with the thin sections by the presence of water, and the possibilities of entraining air under the thin sections is further reduced.

Further, the thin-section scooping tool according to the invention is a tool for scooping thin sections floating on the surface of the liquid bath, and it comprises plural linear bodies disposed in parallel with each other and at intervals narrower than the maximum length of the thin sections.

In accordance with the thin-section scooping tool above, the thin sections floating on the liquid surface of a liquid bath are scooped up by the thin-section scooping tool. In the case there are bubbles under the thin sections, the bubbles are removed from the thus scooped up thin sections. Then, by pushing downward the thin-section scooping tool, the thin sections deprived of bubbles are released again to float on the liquid surface of the liquid bath. In this case, the thin sections which are in the initial stage before being set afloat on the surface of the liquid may themselves be curled or partially contain irregularities, such that they may easily entrain bubbles. However, after they are once floated on the liquid surface, the thin sections are flattened by the surface tension of the liquid. In this manner, when the thin-section scooping tool is pushed downward to set the thin sections afloat again on the surface of the liquid, such a state is realized in which bubbles are scarcely entrained under the thin sections.

Furthermore, because the thin-section scooping tool comprises only the longitudinal linear bodies free from transverse linear bodies, the bubbles can be readily released from the lower side of the thin sections scooped up from the liquid surface. As a result, bubbles can be prevented from being entrained in the case the thin sections are floated again on the liquid surface of the liquid bath.

Further, the thin-section scooping tool comprises plural linear bodies disposed at intervals narrower than the maximum length of the thin sections; thin sections can be scooped by thus disposing the linear bodies at intervals narrower than the maximum length of the thin sections.

The thin-section scooping tool according to the invention is characterized in that the plural linear bodies are provided between a pair of linear-body supporting parts set opposed to each other in a frame, in such a manner that they are disposed in parallel with each other with intervals taken among them.

In accordance with the thin-section scooping tool, the linear bodies are aligned and supported by using the linear body supporting parts of the frame, by which a simple and lightweight constitution is realized.

The thin-section scooping tool according to the invention is characterized in that the plural linear bodies comprise the upper rims of plural plate-like members that are longitudinally disposed.

According to the thin-section scooping tool above, the linear bodies are constructed by the upper rims of plural plate-like members that are longitudinally disposed. Thus, rigid linear bodies can be obtained to improve durability.

In addition, in the case the linear bodies are constituted from simple wires, there occurs a phenomenon as such that a part of the thin sections tightly adhere to each other and get entangled beneath the wires when the thin sections are scooped up. In such a case, a laborious operation is required to remove the entangled thin sections. On the other hand, in the thin-section scooping tool according to the invention, the possibility of causing tight adhesion and entanglement beneath the linear body is very low because plural plate-like members that are longitudinally disposed are used.

The thin-section scooping tool according to the invention is characterized in that the linear bodies are arranged in such a manner that a virtual plane made by connecting them make a convex curved plane that is upward convex.

According to the thin-section scooping tool above, in the case thin sections floating on the liquid surface of a liquid bath are scooped up by using the thin-section scooping tool, the central part of the thin sections can be forcibly stretched.

The thin-section scooping tool of the invention is characterized in that the linear bodies are arranged in such a manner that a virtual plane produced by connecting the linear bodies makes a concave curved plane that is upward concave.

According to the thin-section scooping tool above, in the case the thin-section scooping tool is pushed downward to set afloat again the thin sections that had been once scooped up, the thin sections can be immersed from the central part thereof to the liquid plane, and this prevents air from being entrained into the lower side of the thin sections.

Furthermore, the method for transporting thin sections according to the invention is a method for transporting thin sections using the thin-section conveyor apparatus as claimed in one of claims 1 to 4, which comprises: a step of transporting thin sections to the liquid bath and floating them on the surface of the liquid bath, by forward rotating the conveyor belt and thereby transporting the thin sections that are mounted on the upper plane of the conveyor belt of the thin-section conveyor apparatus; a step of scooping the thin sections that are set afloat on the surface of the liquid, by reverse rotating the conveyor belt to scoop up the thin sections and mounting them on the conveyor belt; and a step of setting the thin sections thus scooped up afloat again on the liquid surface of the liquid bath after transporting them to the liquid bath by forward rotating the conveyor belt.

In accordance with the method for transporting thin sections, even if air is entrained into the lower side of the thin sections in the case thin sections are transported to the liquid bath to set them afloat on the liquid surface by using the conveyor belt, the bubbles that are present under the thin sections can be released and removed when the thin sections are scooped up from the liquid surface by reverse rotating the conveyor belt. Subsequently, the scooped up thin sections are transported to the liquid bath by forward rotating the conveyor belt; in this instance, air is hardly entrained because the conveyor belt itself is already immersed in the liquid and is sufficiently acquainted with the liquid. That is, the bubbles entrained under the thin sections can be effectively removed.

Further, the method for transporting thin sections according to the invention is a method for transporting thin sections using the thin-section conveyor apparatus as claimed in one of claims 1 to 4, comprising: a step of transporting thin sections to the liquid bath and floating them on the surface of the liquid bath, by forward rotating the conveyor belt and thereby transporting the thin sections that are mounted on the upper plane of the conveyor belt of the thin-section conveyor apparatus; a step of scooping the thin sections that are set afloat on the surface of the liquid, by using a thin-section scooping tool comprising a frame having a pair of filament supporting part disposed opposed to each other and the plural linear bodies that are provided between a pair of linear body supporting parts in such a manner that they are disposed in parallel with each other taking intervals among them; and a step of setting afloat again the scooped up thin sections provided inside the thin-section scooping tool by pushing downward the thin-section scooping tool.

In accordance with the method for transporting thin sections, the thin sections once set afloat on the liquid surface is scooped up and drawn out of the liquid plane, and then lowered downward to float it again on the liquid plane. Thus, similar to the method above, the bubbles entrained under the thin sections can be effectively removed.

Furthermore, on floating the thin sections again on the liquid surface after once scooping them up, a thin-section scooping tool is used instead of a conveyor belt. Thus, the thin sections transportation step using the conveyor belt and the thin sections scooping step comprising scooping up the thin sections and floating them again on the liquid plane by using the thin-section scooping tool can be run parallel to shorten the process time.

According to the invention, the conveyor belt comprises parts for mounting thereon the thin sections, in which the density of the transverse linear body is set lower than that of the other places, or which is made of longitudinal linear body alone, to thereby lower the possibilities of entraining water into the lower side of the thin sections.

Furthermore, because the thin sections once set afloat on the surface of the liquid plane can be scooped up and then floated again to the liquid surface after once releasing the bubbles that are entrained into the lower side of the thin sections, the bubbles that are present on the lower side can be effectively removed.

DESCRIPTION OF THE PREFERRED EMBODIMENTS

Example 1

Figure 1:
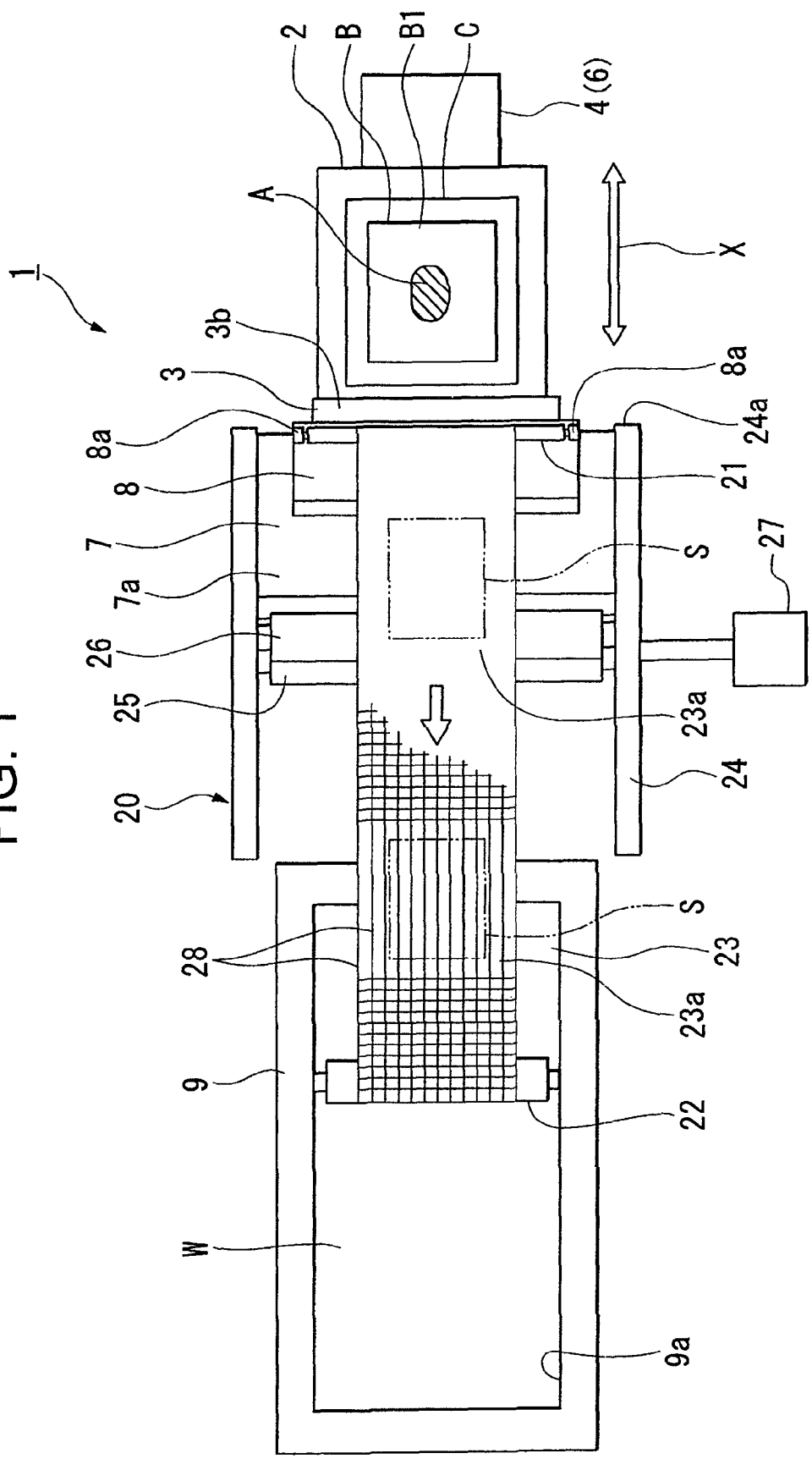
FIG. 1 is a plan view showing a thin-section manufacturing system equipped with a thin-section conveyor apparatus according to a first embodiment of the invention.
Figure 2:
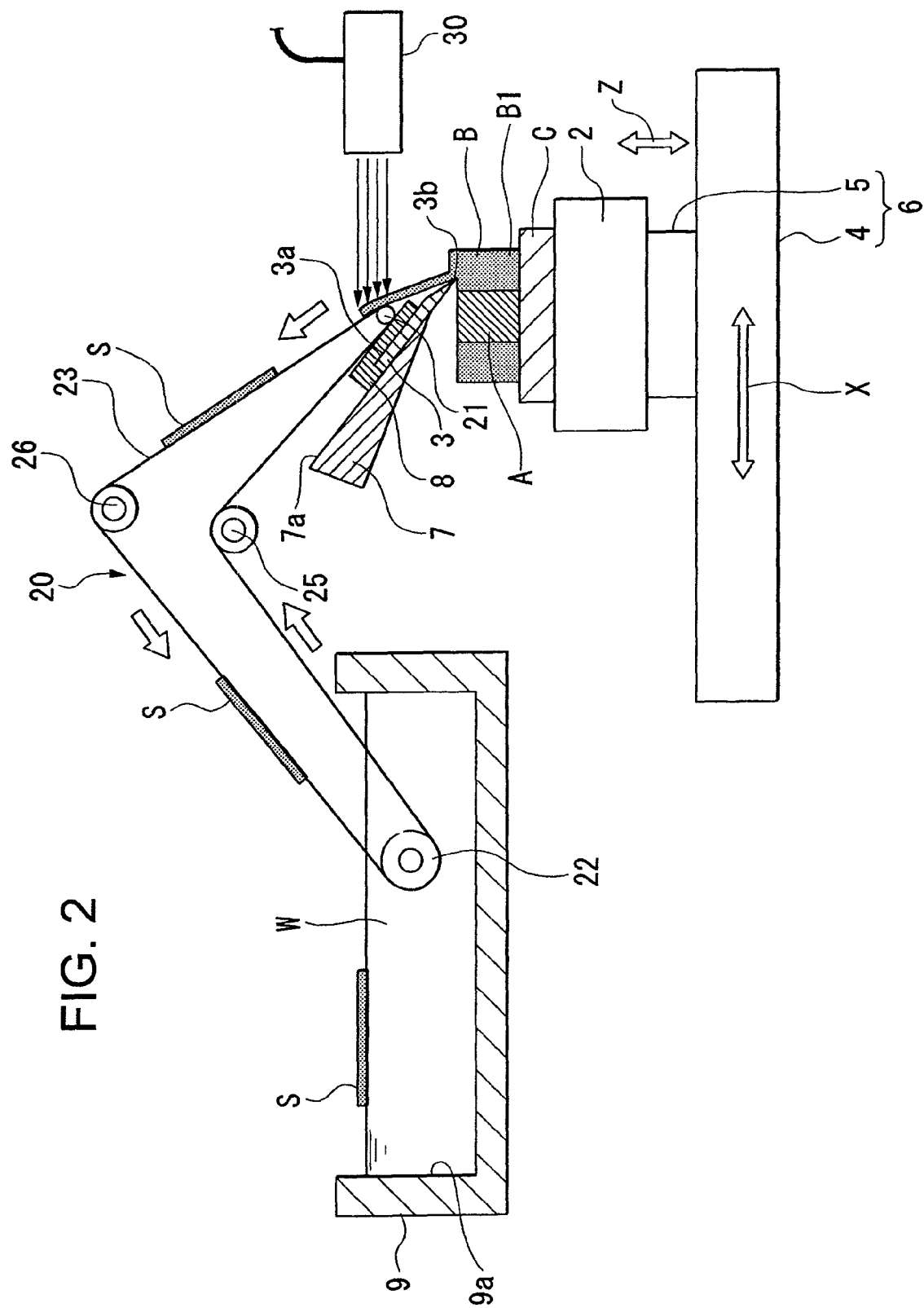
FIG. 2 is a cross section view showing a thin-section manufacturing system equipped with a thin-section conveyor apparatus according to a first embodiment of the invention.

FIGS. 1 and 2 each show a thin-section manufacturing system equipped with a thin-section conveyor apparatus according to the invention, wherein FIG. 1 is a plan view of the thin-section manufacturing system and FIG. 2 is the side view of the thin-section manufacturing system. The thin-section manufacturing system 1 shown in these figures prepares ultra-thin thin sections about 3 to 5 µm in thickness from an embedded block B containing embedded therein a biological sample A, and, in the inspection and observation step for the biological sample A, it automatically cuts out thin sections from the embedded block B and transfers them to the next process step. The biological sample A may be a tissue of an organ and the like that has been taken from human bodies, laboratory animals, and the like, which are properly selected in accordance with the fields of interest, such as medical field, pharmaceutical field, food field, and biological field. The embedded block B is such produced by embedding biological samples A, i.e., surrounding and solidifying the biological sample A with an embedding medium B1. In further detail, such embedded block B is manufactured as follows. First, a block of the biological sample A is immersed in formalin to fix the protein constituting the biological sample A. Then, after solidifying the tissue, the sample is cut into proper size. Finally, internal water of the biological samples A thus cut out is replaced by the embedding medium B1, and the sample is then embedded into a molten embedding medium B1 to solidify. As described above, the embedding medium B1 used herein is a material which is easily capable of being liquefied and then solidified by cooling, and which can be dissolved by immersing into ethanol; such materials include a resin and paraffin. The constitution of the thin-section manufacturing system 1 is described hereinafter.

Referring to FIGS. 1 and 2, the thin-section manufacturing system 1 is equipped with a sample stage 2 for fixing a cassette C having mounted thereon the embedded block B, a cutter 3 for thinly cutting out the embedded block B, and a thin sections transportation apparatus (thin-section conveyor apparatus) 20 for transporting thin sections S that have been thinly cut out from the embedded block B using the cutter 3. The sample stage 2 is capable of positioning and fixing the cassette C having mounted thereon the embedded block B.

Furthermore, a feeding mechanism 6 having an X-stage 4 and a Z-stage 5 is provided to the lower part of the sample stage 2, which is capable of adjusting the position of the embedded block B fixed on the sample stage 2 in the thin cutting direction X (this direction is the same as the direction of transporting thin sections, which is stated hereafter) and the altitude Z, and feeding it to the feeding direction X at a predetermined transportation speed. Furthermore, the thin-section manufacturing system 1 is equipped with a fixing table 7 for supporting the cutter 3, and a holder 8 is provided on the upper plane 7a of the fixing table 7. The holder 8 is brought into contact with the upper plane 3a of the cutter 3 to fix the cutter 3 by sandwiching the cutter 3 with the fixing table 7. The cutter 3 is fixed in such a manner that the cutting direction of the cutting blade 3b provided to the front end may be perpendicular to the feeding direction X. Furthermore, a liquid bath 9 filled with water W is provided to the back of the cutter 3.

The conveyor unit 20 is equipped with a direction switching roller 21 which is provided as a direction switching part in the vicinity of the cutting blade 3b and in the direction approximately in parallel with the direction of the cutting blade 3b, a rear roller 22 provided to the back of the cutter 3, and an endless conveyor belt 23 wound around the direction switching roller 21 and the rear roller 22. Referring to FIG. 1, the direction switching roller 21 and the rear roller 22 are disposed in such a manner that the conveyor belt 23 wound around them may be run approximately in parallel, as viewed in plan view, with the feeding direction X of the feeding mechanism 6. Furthermore, as shown in FIGS. 1 and 2, a pair of supporting members 8a are provided protruded to the upper side on the upper plane of the holder 8. Further, the direction switching roller 21 is axially fixed to the supporting member 8a in a rotatable manner, with a space left out for inserting a conveyor belt 23 with respect to the holder 8 of the cutter 3. The rear roller 22 is fixed with an axis to the inner wall 9a of the liquid bath 9 in a rotatable manner, and is immersed in water W of the liquid bath 9. In addition, intermediate rollers 25 and 26 are provided between the direction switching roller 21 and the rear roller 22, which are axially fixed to a frame 24 in a rotatable manner and located higher than the direction switching roller 21 and the rear roller 22. The fixing table 7 for supporting the cutter 3 is also fixed to the frame 24 by the front edge portion 24a. Furthermore, a motor 27 which functions as a driving unit is connected to the intermediate roller 26.

Specifically, as shown in FIG. 1, by driving the motor 27, the conveyor belt 23 of the conveyor unit 20 runs endlessly in such a manner that, by plan view, its running direction be approximately in parallel with the feeding direction X of the feeding mechanism 6. More specifically, as shown in FIG. 2, the conveyor belt 23 runs from the rear roller 22 provided to the back of the cutter 3 to the cutter 3, then runs through the interstice between the direction switching roller 21 and the holder 8 via the intermediate roller 25, and is guided to the position in the vicinity of the cutting blade 3b of the cutter 3. Then, after it is bent upward by the direction switching roller 21 and via the intermediate roller 26, the conveyor belt 23 is wound back to the back of the cutter 3 by the rear roller 22. The revolutions of the motor 27 is set in such a manner that the running speed of the conveyor belt 23 be approximately equal to the transportation speed in the feeding direction X of the feeding mechanism 6.

Figure 3:
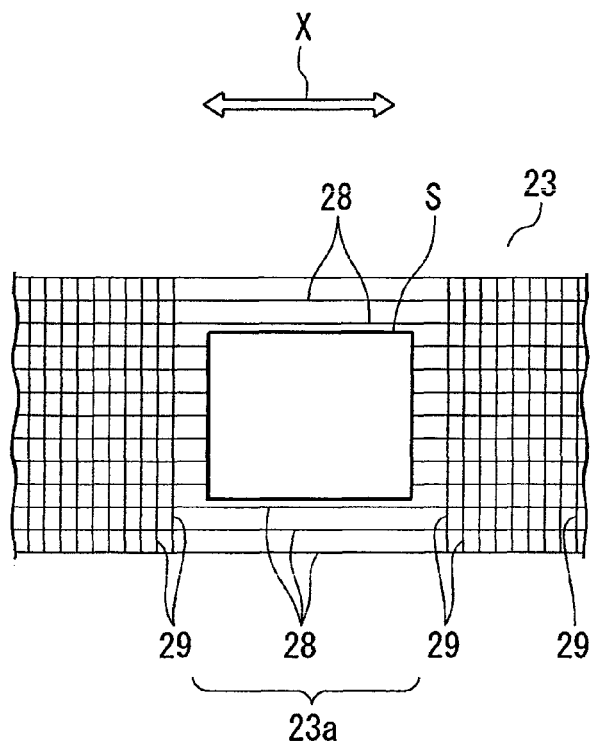
FIG. 3 is a plan view showing the key part of a conveyor belt utilized in a first embodiment of the invention.

Here, the conveyor belt 23 comprises, as shown in FIG. 3, a warp (a linear body in the longitudinal direction) 28 extended in the direction of transportation X and a weft (a linear body in the transverse direction) 29 extended in the direction perpendicular to the warp 28. The part 23a for mounting thin sections S of the conveyor belt 23 is made only from warp 28 and is free of weft 29.

In order to easily take up water, the warp 28 and the weft 29 are preferably made of materials having hydrophilicity, such as those having a hydroxyl group, a carboxyl group, an amino group, or a carbonyl group.

An air blower 30 is provided to the position faced to the first bending axis 22 located at the front of the cutter 3.

Then, the function of the thin-section manufacturing system 1 equipped with the thin-section conveyor apparatus according to the present embodiment is described below. Referring to FIG. 2, the embedded block B is position adjusted in the altitude direction Z by using the Z-stage 5 of the feeding mechanism 6 to determine the relative positions of the cutter 3 and the embedded block B, such that the embedded block B can be thinly cut with the cutter 3 at a predetermined thickness (in a thickness of from about 3 to 5 μm). Then, by driving the X-stage 4 of the feeding mechanism 6, the embedded block B fixed to the sample stage 2 is moved along the feeding direction X at a predetermined transportation speed, while driving the motor 27 to run the conveyor belt 23. Since the cutter 3 is fixed to the frame 24 of the conveyor unit 20 by the fixing table 7, the embedded block B is moved relatively with respect to the cutter 3 and the conveyor unit 20. Then, as shown in FIG. 2, the cutter 3 thinly cuts the embedded block B to produce thin sections S. In this case, since the surface B2 of the embedded block B remains free from being pressed or the like, there is no possibilities of causing deformation on the surface B2 of the embedded block B, and thin cutting can be carried out under observation of the surface B2. Thus, thin cutting of the embedded block B is conducted accurately and at a uniform thickness. The thin sections S thus prepared are shaved upward by the cutter 3 and moved to the back of the cutter 3.

Then, since the direction switching roller 21 is provided to the upper side of the cutter 3 and in the vicinity of the cutting blade 3b, as the thin section S moves to the back of the cutter 3, the front edge of the thin section S is bent by the direction switching roller 21 and brought into contact with the conveyor belt 23 that is wound back to the feeding direction X. Furthermore, by thus continuously producing the thin sections S with the cutter 3, the thin sections S thus produced are mounted on the conveyor belt 23 running to the back of the cutter 3.

In this case, the rotation of the motor 27 and the drive of the X stage 4 using the feeding mechanism 6 are synchronized in such a manner that the thin sections S may be mounted on the predetermined part 23a.

Air is blown by an air blower 30 to the thin sections S thus thinly cut by the cutter 3, such that the thin sections S may be pressed against the conveyor belt 23 which is bent by the direction switching roller 21. In this manner, the thin sections S produced by the cutter 3 are more reliably mounted on the conveyor belt 23, and are transported by the conveyor belt 23 to the back of the cutter 3. In particular, on thinly cutting with the cutter 3, there are cases in which the thin sections S are curled to the front of the cutter 3; however, curling can be prevented from occurring by thus blowing air with the air blower 30.

Then, by completely cutting thinly the embedded block B with the cutter 3, the thin sections S are cut apart from the embedded block B and transported together with the conveyor belt 23 to the back of the cutter 3. The running speed of the conveyor belt 23 is approximately the same with the moving speed of the feeding mechanism 6, i.e., the speed of producing the thin sections S with the cutter 3. Thus, the thin sections S thus produced are free from being pulled or torn by the conveyor belt 23 in such cases that the running speed of the conveyor belt 23 is too fast. On the contrary, even in the case the running speed of the conveyor belt 23 is slow, the thin sections S remain free from wrinkles that may be caused between the conveyor belt 23 and the cutting blade 3b of the cutter 3.

Thus, by being transported to the position of the rear roller 22, the thin sections S mounted on the conveyor belt 23 are further carried to water W of the liquid bath 9 together with the conveyor belt 23, where they are released from the conveyor belt 23 and set afloat on the surface of the water.

In the case the thin sections S are transported to the liquid bath 9 by the conveyor belt 23, the warp 28 extended along the direction of transportation of the conveyor belt 23 gradually intrudes from the front end into the water contained in the liquid bath 9. Thus, because the fibers of the warp 28 are gradually immersed with water, the wasp 28 is fundamentally less entrained with air. In contrast to this, the weft 29, which is perpendicular to the direction of transportation of the conveyor belt 23, is wholly immersed at once in the water in the liquid bath 9. Accordingly, the fibers of the weft 29 are soaked with water W for an extremely short time, and this leads to a result of easily entraining air. In addition, the presence of the weft 29 generates irregularities at the crossing parts of the warp 28 and weft 29, which thereby generate irregularities on the warps 28 and wefts 29 themselves. The formation of such irregularities also facilitates air entrainment.

The portion 23a for mounting thin sections S on the conveyor belt 23 is made only of warps 28 and has no wefts 29. That is, because the wefts 29, which are apt to entrain air on immersion into water, are omitted, the air entraining ratio can be lowered; as a result, the possibilities of entraining air under the thin sections S that are being transported by the conveyor belt 23 can be reduced.

Furthermore, deformations such as wrinkles, warping, and strain, which were generated on the thin sections S during thin cutting can be corrected when the thin sections S are floated on water S in the liquid bath 9 because of the surface tension effected by water.

Figure 4:
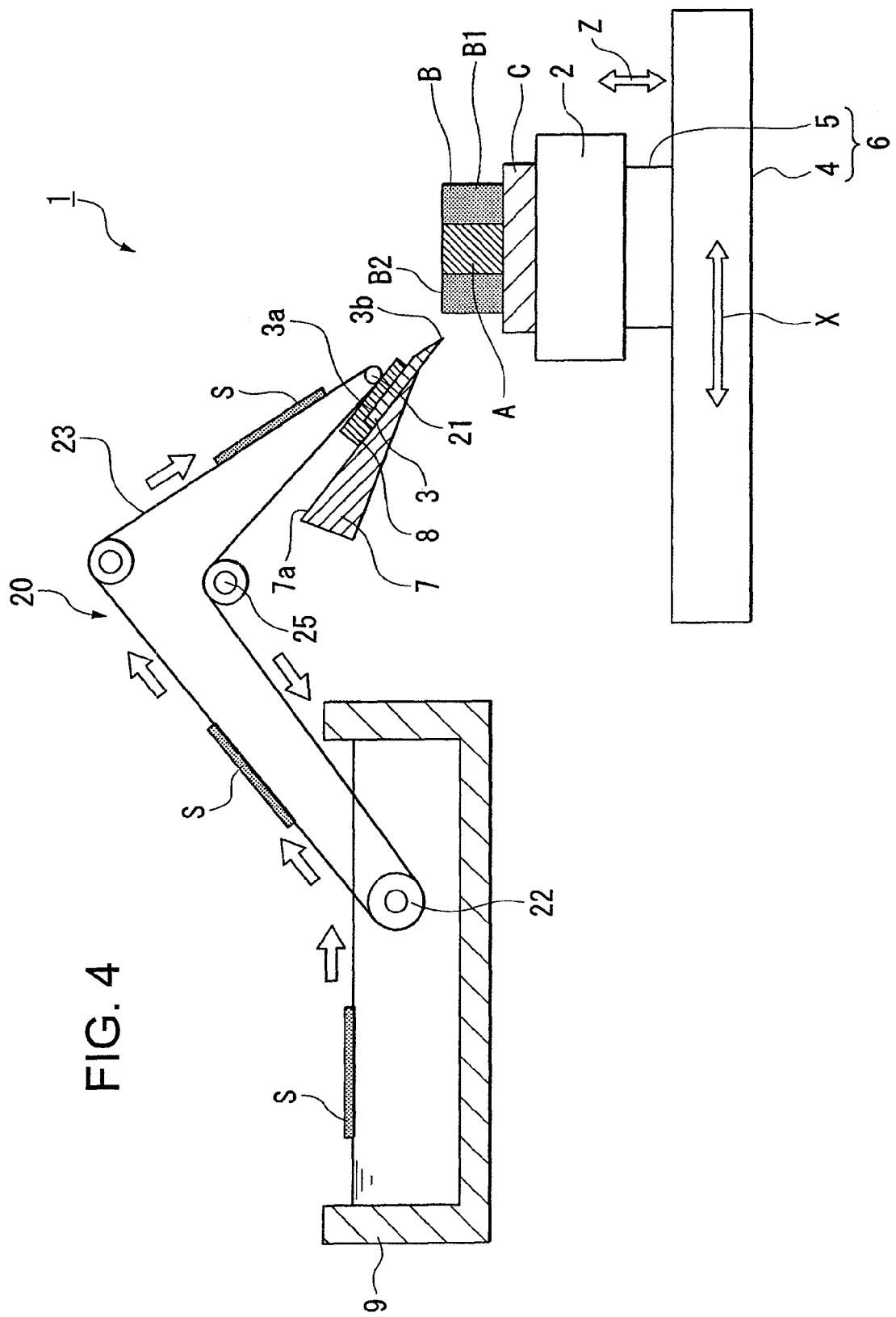
FIG. 4 is an explanatory figure showing the operation of the first embodiment of the invention.

After setting afloat the thin section S on the water surface for some flattening and upon passage of a predetermined time, the conveyor belt 23 that had been once stopped is reverse rotated as shown in FIG. 4. At this moment, the reverse rotation of the conveyor belt 23 induces flow in the water W inside the liquid bath 9, and this flow of water W attracts the thin section S to the side of the conveyor belt, such that the edge portion finally mount on the conveyor belt 23. Then, with further rotating the conveyor belt 23 reversely, the entire thin section S is scooped up on the conveyor belt 23. At this instance, the part of the conveyor belt 23 which scoops is made of warps 28 alone. As a result, because the thin section S is somewhat flattened and the attracting part of the conveyor belt 23 is made of warps 28 alone, the bubbles are immediately released even if there should be bubbles entrained under the thin section.

Subsequently, the conveyor belt 23 is once stopped, and forward rotated again after passage of a predetermined time (for instance, 5 to 20 seconds). The thin sections S that have been scooped up are immersed again into the water W of the liquid bath 9 by the forward rotation of the conveyor belt 23. At this instance, the conveyor belt 23 is already well acquainted with water, and hence, bubbles are prevented from being entrained. In addition, the thin section S itself is flattened and further prevents bubbles from being entrained.

As a result, bubbles are prevented from being entrained into the lower side of the thin sections S, and even if they should be entrained, the bubbles can be immediately removed.

Modified Example

In the first embodiment, the conveyor belt 23 comprises a part 23a for mounting thin sections on the conveyor belt 23, which is made of warps 28 alone; however, the invention is not only limited thereto, and the part 23a for mounting the thin sections on the conveyor belt 23 may be such having wefts 29 at a density lower than in the other parts.

Figure 5:
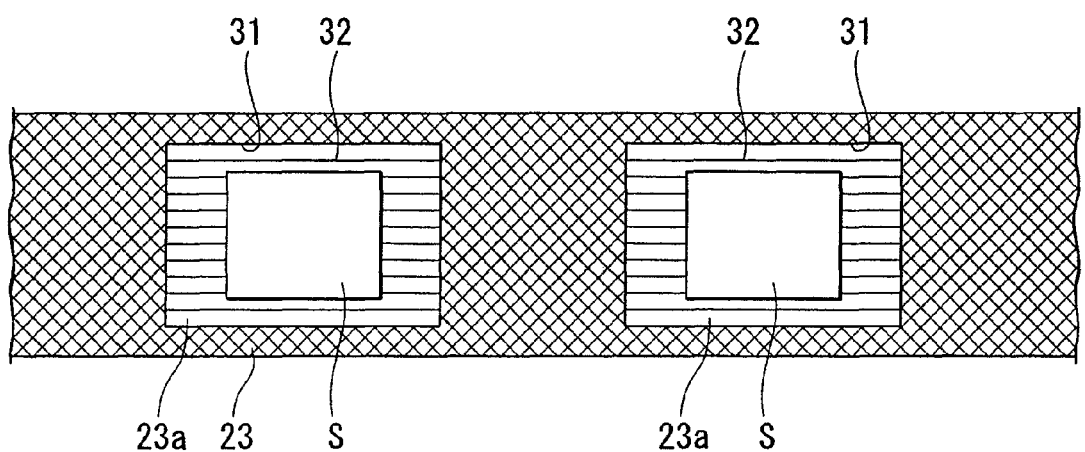
FIG. 5 is a plan view of a conveyor belt according to a modification of the first embodiment of the invention.

Furthermore, in the first embodiment above, the part 23a for mounting thin sections S was made solely of the warps 28 which constitute the conveyor belt 23; however, the invention is not only limited thereto, and the part 23a for mounting thin sections S thereon may be constituted, as shown in FIG. 5, by perforating a hole 31 in a part of the conveyor belt 23, and attaching warps (linear body) 32 extended along the direction of transportation of the conveyor belt 23, in such a manner that they may be disposed in parallel and with predetermined intervals taken among them. In this case, the conveyor belt 23 need not be a cloth, but films or mesh type fabrics can be used without any limitations concerning the material.

The warps 32 in this modified example and the warps 28 referred in FIG. 1 above were both constituted with a thread, however, the member constituting the part 23a for mounting thereon the thin sections S need not be a thread, and also usable are linear bodies such as films cut into linear shapes, resin monofilaments spun out from an intruder, such as fishing lines, and metallic monofilaments. This applies as well in the second and the third embodiments that are described hereinafter.

Example 2

Figure 6:
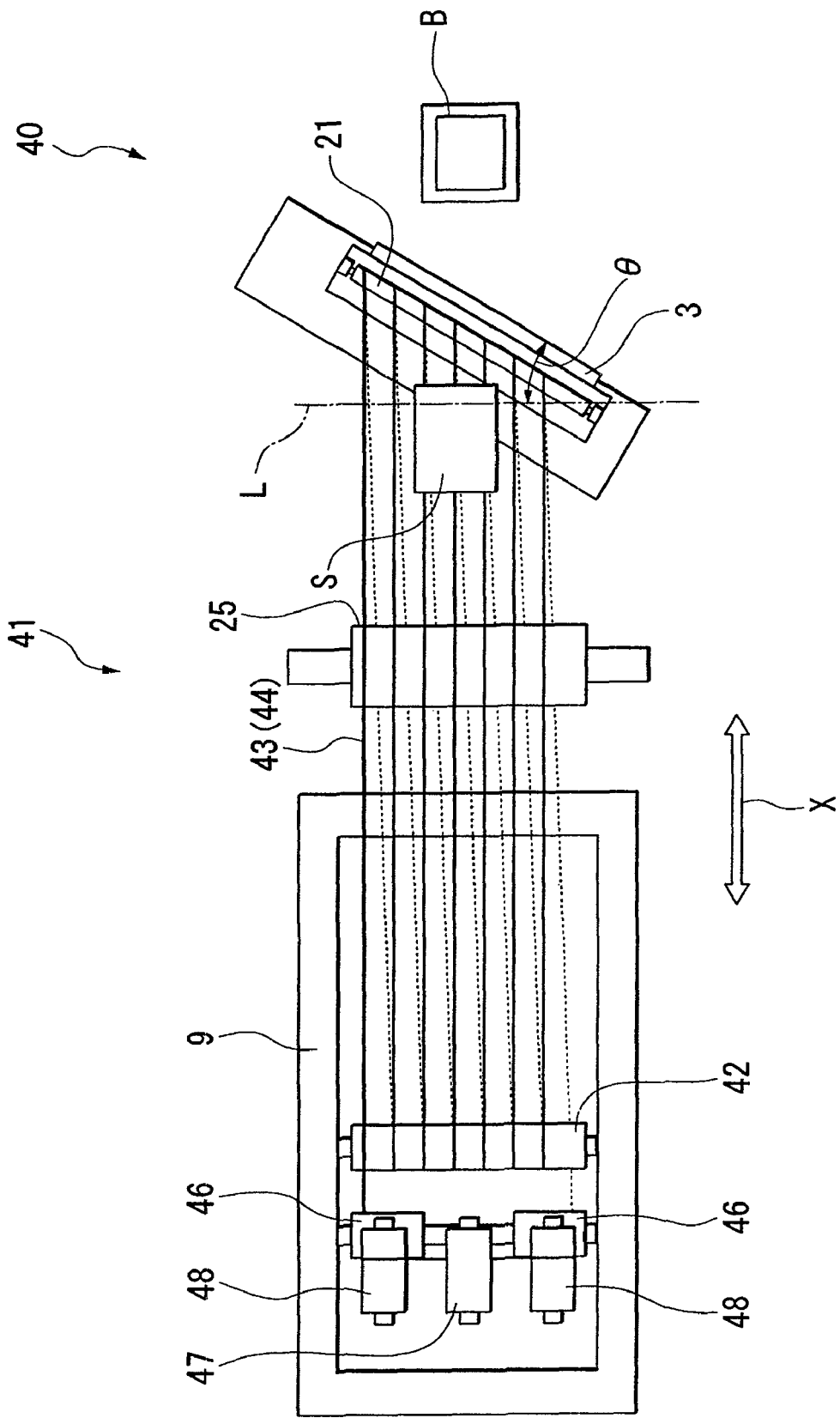
FIG. 6 is a plan view showing a thin-section manufacturing system equipped with a thin-section conveyor apparatus according to a second embodiment of the invention.
Figure 7:
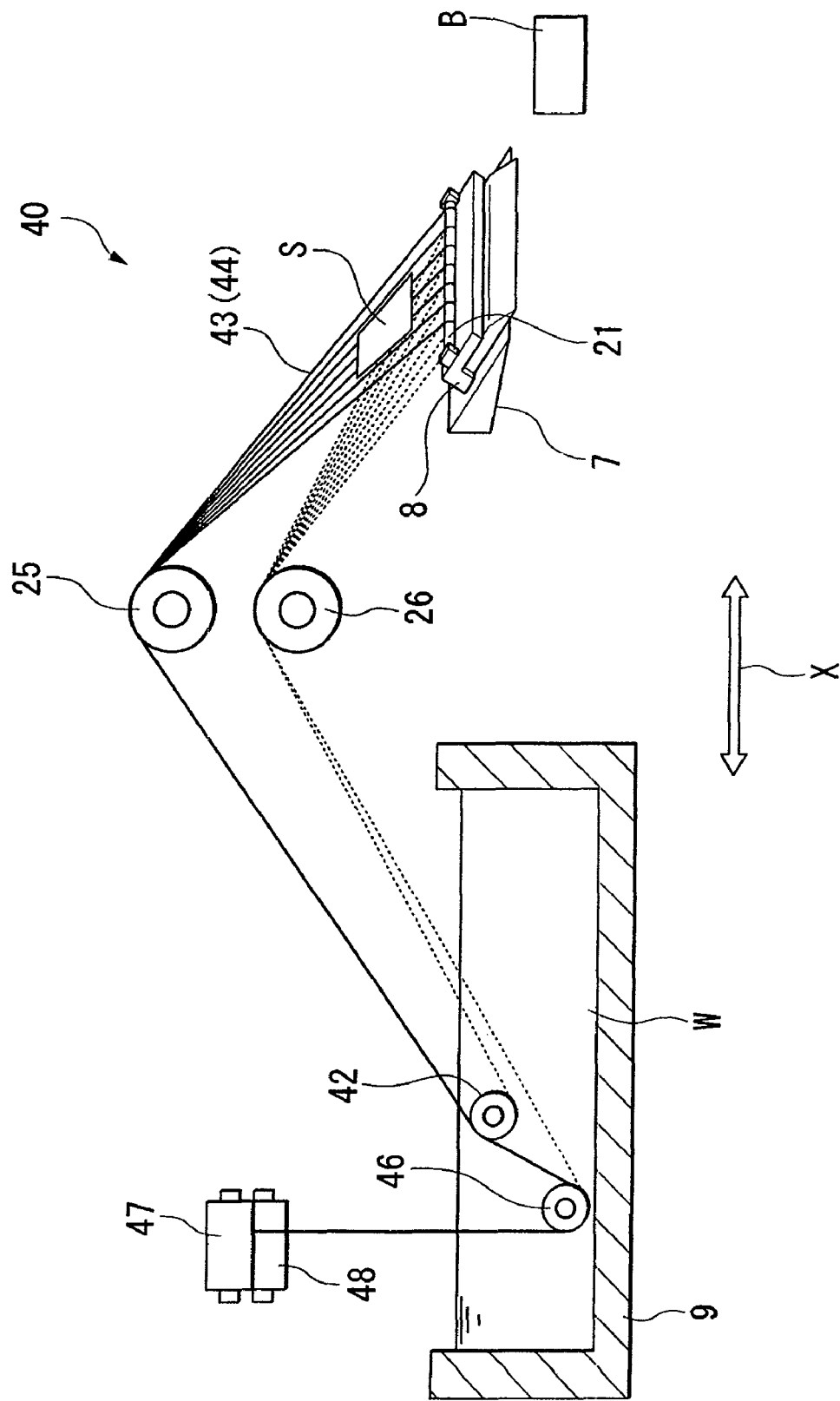
FIG. 7 is a side view showing a thin-section manufacturing system equipped with a thin-section conveyor apparatus according to a second embodiment of the invention.

FIGS. 6 and 7 show a thin-section manufacturing system equipped with a thin-section conveyor apparatus according to the invention. FIG. 6 is a plan view, and FIG. 7 is a side view partially cross sectioned. In the present embodiment, the same members as those used in the aforementioned examples are indicated with the same symbols to omit their explanations.

Referring to FIG. 6, the thin-section manufacturing system 40 described in the present embodiment comprises a cutter 3 provided at a draw angle θ with respect to the axial line L perpendicular to the direction of transportation X. The conveyor unit (thin-section conveyor apparatus) 41 is equipped with a direction switching roller (starting point roller) 21 and a rear roller (ending point roller) 42, and a conveyor belt 43 wound around the rollers 21 and 42. Furthermore, the rear roller 42 is axially fixed in a rotatable manner to a frame not shown, and supports conveyor belt 43 so that the belt may be run in the direction of transportation X. The conveyor belt 43 is formed by spirally winding a single warp (linear body) 44 around the direction switching roller 21 and the rear roller 42 with intermediate rollers 25 and 26 interposed therein, in such a manner that the warps may be extended in parallel with each other taking intervals along the direction of transportation.

Further, in the back of the rear roller 42, a direction switching roller 46 and a driving roller 47 disposed to the upper side of the direction switching roller 46 are interposed between the idle rollers 48 and 48, and the warp 44 wound around the rear roller is partly passed through these rollers 46, 47, and 48 and returned back to the rear roller 42. The driving roller 48 and the idle roller 48 are disposed as such that their axial line is in parallel with the direction of transportation X. Thus, by driving the driving roller 47 with a motor not shown, transportation force is imparted to the warp 44, and the warp 44 thus having the transportation force is sent to the rear roller 42 via the idle roller 48 and the direction switching roller 46, where the warp reciprocates for several times between the rear roller 42 and the direction switching roller 21. Then, the warp reaches the direction switching roller 46, and returns back to the driving roller 47 via the idle roller 48.

In the thin-section manufacturing system 40 above, the conveyor belt 43 is made basically of warp 44 alone. Accordingly, air can be prevented from being entrained in case the thin sections S are transported and immersed into the liquid bath 9. Furthermore, since the conveyor belt 43 is constructed by a single warp 44, the tensile force is automatically homogenized and need not be adjusted among the plural warps disposed between the direction switching roller 21 and the rear roller 42.

In this embodiment again, the thin sections S once floated on water may be scooped up with the conveyor belt 43 and set afloat again in water by sequentially rotating the conveyor belt 43 in the order of forward rotation, reverse rotation, and forward rotation.

Example 3

Figure 8:
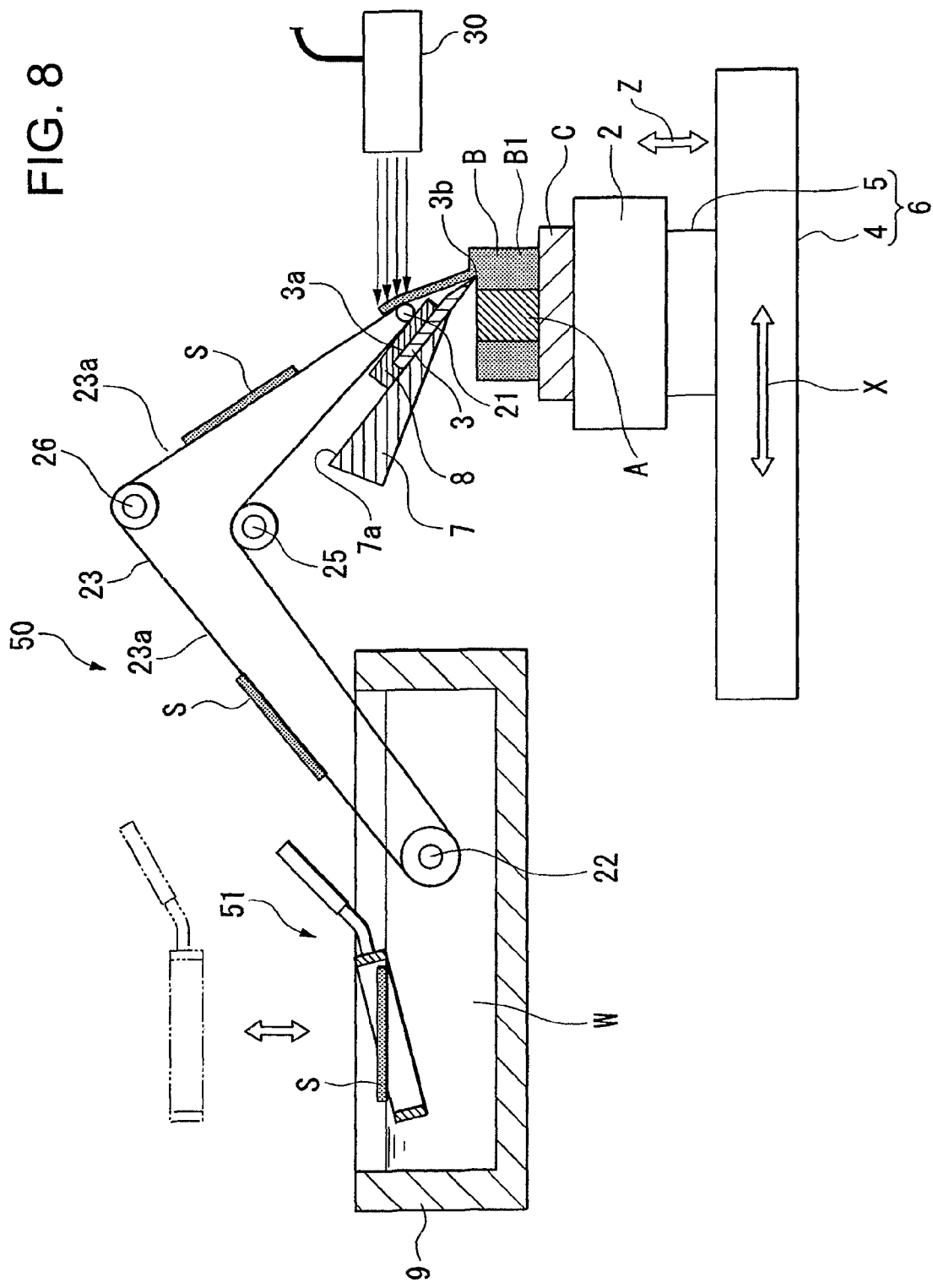
FIG. 8 is a cross section view showing a thin-section manufacturing system equipped with a thin-section conveyor apparatus according to a third embodiment of the invention.
Figure 9:
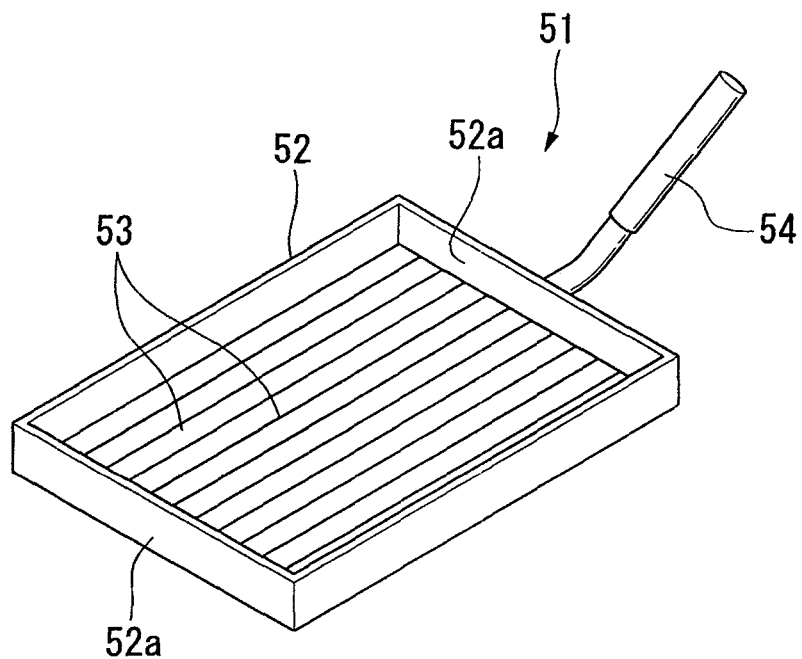
FIG. 9 is an oblique view of a thin-section scooping tool utilized in the third embodiment of the invention.

FIGS. 8 and 9 show a thin-section manufacturing system equipped with a thin-section conveyor apparatus according to the invention. In this embodiment, the same members used in Example 1 above are indicated by the same symbols that were used in Example 1 to omit the description.

Referring to FIG. 8, the thin-section manufacturing system 50 according to the present embodiment comprises a special thin-section scooping tool 51 separately from the conveyor belt 23 to scoop the thin sections S which are floated on the liquid surface of the liquid bath 9. As shown in FIG. 9, the thin-section scooping tool 51 comprises a frame 52 having an opposed pair of thread supporting parts 52a, 52a (linear body supporting part), and plural warps (linear body) 53 provided between them, each in parallel with each other and disposed at an interval smaller than the diameter of the thin sections to be scooped up. A handle 54 is also provided.

In this embodiment, a planar rectangular frame was used, but the shape of the frame is not only limited thereto, and may be circular, oval, or polygonal shapes other than four sided ones; that is, any shape having an opposed pair of thread supporting parts 52a, 52a can be used as well.

In the method for transporting thin sections using the thin-section manufacturing system 50 above, the thin sections S mounted on the upper side of a conveyor belt 23 is transported to the liquid bath 9 by forward rotating the conveyor belt 23 and set afloat in water W. This process is the similar to the transportation method described in Example 1.

In the present embodiment, the thin-section scooping tool 51 is used to scoop up the thin sections S from the surface of the water W. In this case, if there are bubbles under the thin sections S, the bubbles are removed from the thus scooped up thin sections S. Then, by downward pushing the thin-section scooping tool 51, the thin sections S thus scooped up into the thin-section scooping tool are set afloat again on the water inside the liquid bath 9.

In accordance with the method for transporting thin sections, the thin sections S once floated on the surface of the liquid is scooped out from the liquid surface and then lowered down to set afloat on the liquid surface. Accordingly, similar to the case described in Example 1, the bubbles entrained under the thin sections S can be effectively removed.

Furthermore, because scooping up of the thin sections S and floating them on the liquid surface are carried out by using a thin-section scooping tool 51 instead of the conveyor belt 23, the transportation step of the thin sections using the conveyor belt 23 and the steps of scooping up the thin sections using the thin-section scooping tool 51 and the subsequent step of floating them on the liquid surface can be carried out simultaneously as parallel steps to shorten the time of processing.

The thin-section scooping tool 51 described above uses plural warps 53; however, the invention is not only limited thereto, and as the warp of the conveyor belt 43 according to Example 2, a single warp may be wound spirally to form a shape.

Figure 10:
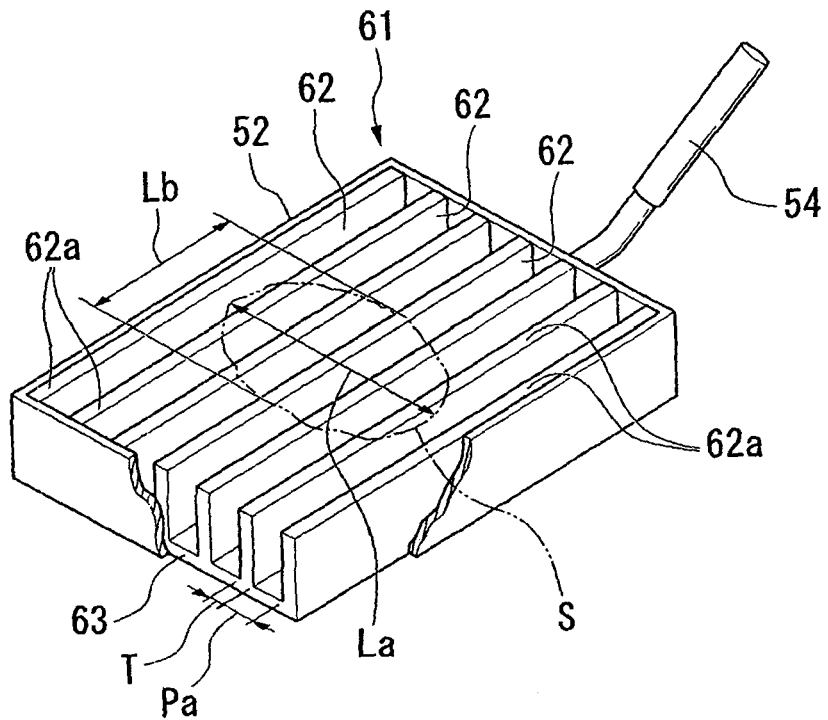
FIG. 10 is an oblique view of another thin-section scooping tool utilized in the third embodiment of the invention.

FIG. 10 is an oblique view of another example of a thin-section scooping tool.

The thin-section scooping tool 61 comprises a frame 52, in which plural platy members 62 are longitudinally disposed in parallel with each other by taking an interval among them that is narrower than the maximum length La of the thin sections S. The linear body for scooping up the thin sections is constructed by the upper rim portion 62a of the thus lined up platy members 62. Furthermore, the lower ends of the platy members 62 are connected with each other by a common bottom plate 63.

In the case the pitch Pa of the plural platy members 62 are narrower than the maximum length La of the thin sections S, as described above, the thin sections S can be scooped with the thin-section scooping tool 61 by taking into account the direction of the thin-section scooping tool 61 with respect to the thin sections S. However, on considering the practical efficiency of handling, the pitch Pa of the plural platy members 62 is preferably set narrower than the minimum length Lb of the thin sections S.

More specifically, the pitch Pa of the platy members 62 is preferably set in a range of from about 0.2 mm to 5 mm. If the pitch Pa should be smaller than this range, the air incorporated under the thin sections cannot be easily released; if the pitch should be larger than this range, the parts for supporting the thin sections tend to be widely opened, and this may apply an excessive load to the thin sections on scooping them up. The thickness T of the platy members 82 is preferably in the range of from about 10 μm to 100 μm. If the thickness should be thinner than this range, the part supporting the thin sections become too narrow as to unfavorably apply excessive load on scooping the thin sections; if the thickness should be thicker than this range, the air incorporated under the thin sections cannot be easily released.

In accordance with the thin-section scooping tool 61, the upper rim portions 62a of the plural longitudinally disposed platy members 62 constitute a linear body so as to obtain a rigid linear body having excellent durability.

Furthermore, in case of constituting the linear body with simple warps (wire materials) as shown in FIG. 9 for scooping the thin sections, parts of the thin sections tightly adhere with each other to cause entanglements on the lower side of the wire materials in the case the are scooped up. In such a case, a laborious operation is required to remove the entangled thin sections. On the other hand, the thin-section scooping tool 61 as shown in the figure facilitates handling because the possibility of causing tight adhesion and entanglement under the linear body constituted by the upper rim portions 62a of the platy members 62 is very low since plural plate-like members 62 that are longitudinally disposed are used.

Figure 11:
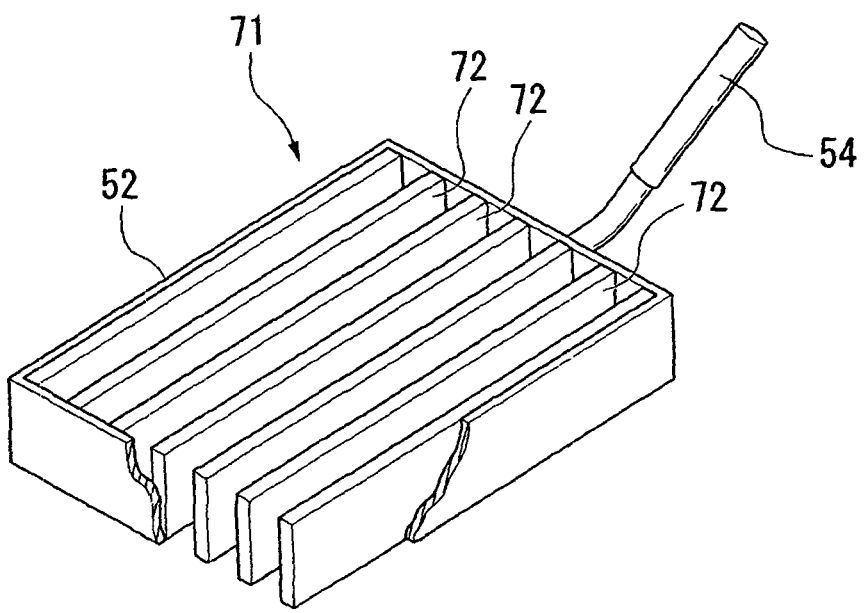
FIG. 11 is an oblique view of a still other thin-section scooping tool utilized in the third embodiment of the invention.

FIG. 11 is an oblique view of another example of a thin-section scooping tool.

The thin-section scooping tool 71 differs from the one shown in FIG. 10 in that it lacks a common bottom plate for connecting the lower ends of the platy members 72. The positions of the platy members 72 are fixed because the both ends in the longitudinal direction are each fixed to the frame 52. The thin-section scooping tool 71 also provides a similar effect as that of the thin-section scooping tool 61 shown in FIG. 10.

Figure 12:
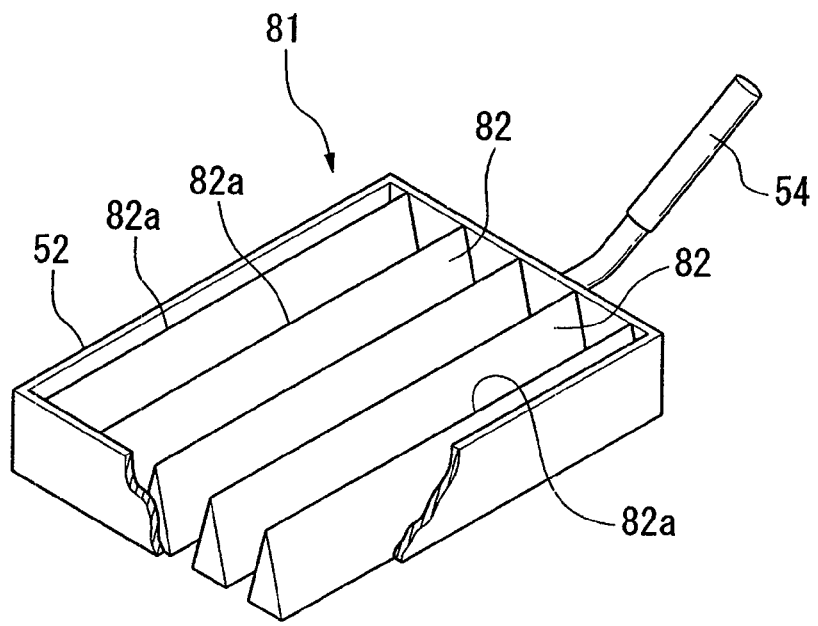
FIG. 12 is an oblique view of a yet other thin-section scooping tool utilized in the third embodiment of the invention.

FIG. 12 is an oblique view of a still other example of a thin-section scooping tool.

The thin-section scooping tool 81 differs from the one shown in FIG. 11 in that the shape of each platy member 82 has a triangular cross section, which is narrower for the upper part.

By adopting such a constitution, the upper rim portion 82a of the platy members 82 constituting the linear body can be fabricated as thinly as possible, while simultaneously satisfying the requirement of maintaining the rigidity of the platy members 82 as high as possible.

Figure 13:
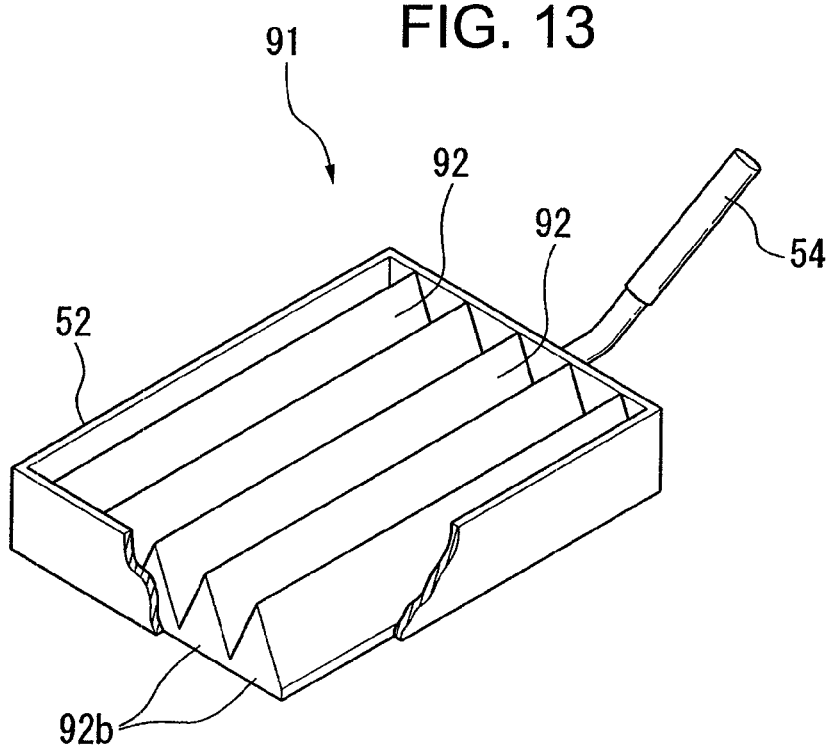
FIG. 13 is an oblique view of a further other thin-section scooping tool utilized in the third embodiment of the invention.

FIG. 13 is an oblique view of a yet other example of a thin-section scooping tool.

The thin-section scooping tool 91 differs from the one shown in FIG. 12 above in that the bottom parts 92b of the platy members 92, which are each formed into a shape with triangular cross section, are connected with each other.

Such a constitution further increases the rigidity of the platy members 92.

Figure 14:
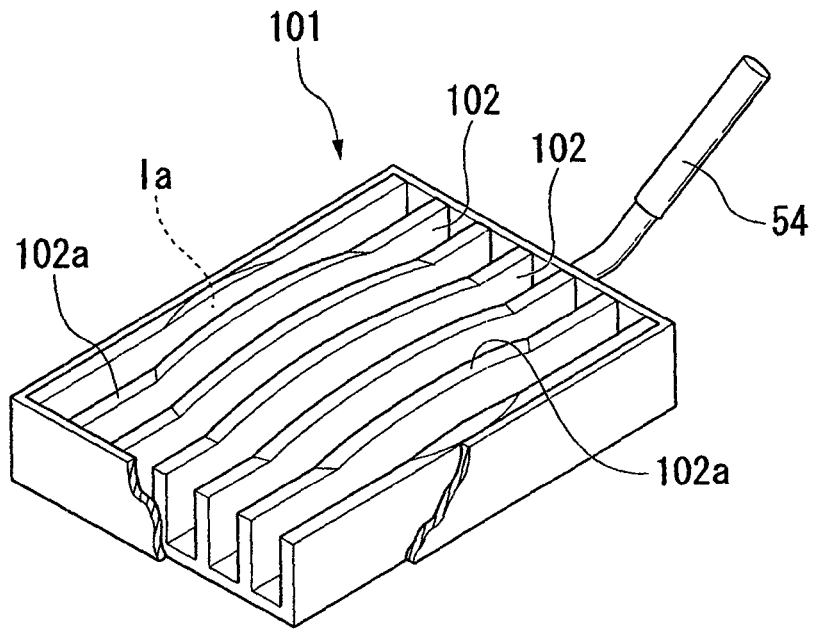
FIG. 14 is an oblique view of a still yet other thin-section scooping tool utilized in the third embodiment of the invention.

FIG. 14 is an oblique view of a further other example of a thin-section scooping tool.

The thin-section scooping tool 101 differs from the one shown in FIG. 10 above in the shape of the upper rim portions 102a of the platy members 102 which provides the linear body.

More specifically, in the thin-section scooping tool of FIG. 10, the virtual plane obtained by connecting the upper rim portions 62a of the platy members 62 was a simple flat plane, whereas in the thin-section scooping tool 101, the virtual plane Ia obtained by connecting the upper rim portions 102a of the platy members 102 exhibits a convex curved plane that is upward convex.

Such a constitution enables forced flattening of the necessary portions of the slightly shrunk thin sections on scooping up the thin sections floating on the liquid surface of the liquid bath by using the thin-section scooping tool 101; the convex curved virtual plane generated by connecting the upper rim portions 102a of the platy members 102 forcibly flattens the necessary parts, such as the central parts, of the shrunk thin sections.

Figure 15:
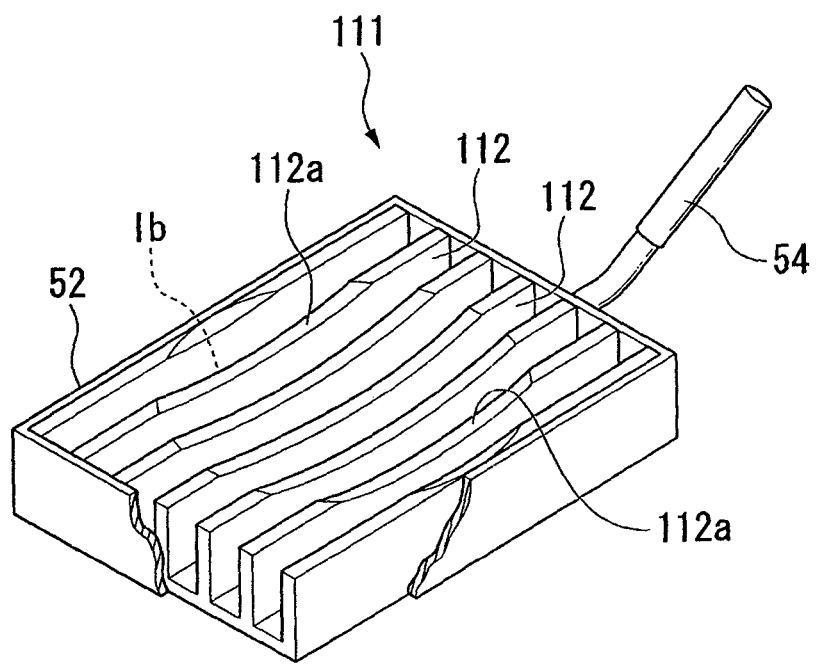
FIG. 15 is an oblique view of another thin-section scooping tool utilized in the third embodiment of the invention.

FIG. 15 is an oblique view of a yet other example of a thin-section scooping tool.

In the thin-section scooping tool 111, the virtual plane Ib obtained by connecting the upper rim portions 112a of the platy members 112 exhibits a concave curved plane that is upward concave.

By employing such a constitution, in the case the thin-section scooping tool 111 is pushed downward to set the once scooped up thin sections afloat on the liquid surface, the thin sections may be immersed, for instance, from the central part thereof, so as to prevent air from being entrained under the thin section.

Figure 16:
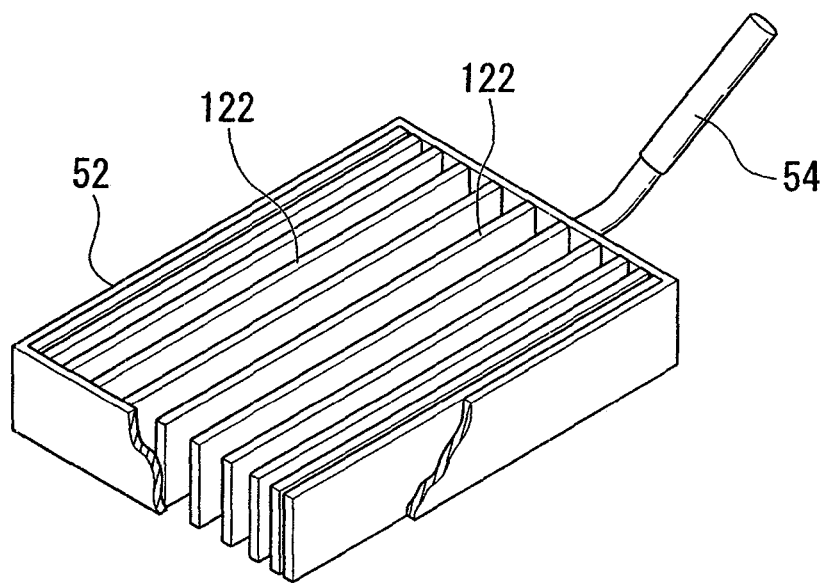
FIG. 16 is an oblique view of another thin-section scooping tool utilized in the third embodiment of the invention.

FIG. 16 is an oblique view of a further other example of a thin-section scooping tool.

The thin-section scooping tool 121 differs from the one shown in FIG. 10 above in the pitch of the plural platy members 122 disposed in parallel with each other with an interval taken among them.

More specifically, the thin-section scooping tool shown in FIG. 10 comprises plural platy members 62 at a pitch that is set uniform regardless of whether it is in the central part or in the edge part. However, in the thin-section scooping tool 121, the pitch of the plural platy members 122 is set to be the largest at the center and to gradually reduce from the center to the edges.

That is, in the thin-section scooping tool 121, the number of the platy members 122 is decreased at the central part, to thereby correspond to the requirement of preventing air from being entrained on scooping the thin sections, and the number of the platy members 122 is increased at the edge parts, to thereby correspond to the needs of assuring the supporting strength better than preventing the air entrainment; in this manner, optimal support can be provided on scooping out the thin sections from the surface of the liquid.

The thin-section scooping tools each described with respect to FIGS. 9 to 16 are all equipped with a frame 52; among them, the thin-section scooping tools shown in FIGS. 10, 13, 14, and 15 comprise platy members the lower ends of which are connected with each other. Accordingly, the frame is not always a necessary member, so the frame may be omitted and a handle 54 may be directly attached to the connected platy members.

Furthermore, for those forming a convex curved virtual plane Ia obtained by connecting the upper rim portions of the platy members 102 as shown in FIG. 14, a concave curved virtual plane Ib obtained by connecting the upper rim portions of the platy members 112 as shown in FIG. 15, or for such having the pitch of the platy members 122 differed for the central part and the edge part as shown in FIG. 16, the platy members need not be such having a rectangular cross section, and those having a triangular cross section are well applicable. In addition, it is also applicable to those using wire materials for constituting a linear body as shown in FIG. 9.

Further, these thin-section scooping tools are usable not only for direct operation by humans, but also for automatic operation using a controller, for instance, by attaching it to the front end of a robot arm.

The embodiments of the present invention have been described in detail by making reference to drawings, but the practical constitution is not only limited to the embodiments above, and design modifications are also included in the present invention so long as they do not deviate from the scope of the invention.

Furthermore, the transfer speed of the feeding mechanism 6 was set approximately equal to the running speed of the belt; so long as thin sections S are transported by mounting them on a conveyor belt, the speeds should be mutually adjusted so that the thin sections S should not be damaged.

In addition, a liquid bath 9 filled with water W was assumed; however, the liquid to be contained in the liquid bath 9 need not be water but any liquid based on water is usable, and so long as the liquid does not dissolve the embedding medium B1, various types of liquids may well be selected.

What is claimed is:

1. A thin-section conveyor apparatus for transporting thin sections, comprising:
    an embedded block that thinly cuts and prepares the thin sections and transports the thin sections to a liquid bath;
    a conveyor belt for mounting the thin sections on the upper plane, the conveyor belt having a plurality of longitudinal linear bodies extended along the direction of transportation and a plurality of transverse linear bodies disposed perpendicular to the longitudinal linear bodies,
    wherein the density of the transverse linear bodies is lower in an area of the conveyor belt on which the thin sections are to be mounted than in remaining areas of the conveyor belt; and
    wherein the conveyor belt is hydrophilic.

2. A thin-section conveyor apparatus for transporting thin sections, comprising:
    an embedded block that thinly cuts and prepares the thin sections and transports the thin sections to a liquid bath;
    a conveyor belt for mounting the thin sections on an upper plane,
    wherein an area of the conveyor belt on which the thin sections are to be mounted comprises only of a plural linear bodies extended along the transporting direction of the conveyor belt; and
    wherein the conveyor belt is hydrophilic.

3. A thin-section conveyor apparatus for transporting thin sections, comprising:
    an embedded block that thinly cuts and prepares the thin sections and transports the thin sections to a liquid bath; and
    a conveyor belt for mounting the thin sections on the upper plane of a conveyor belt;
    wherein the conveyor belt comprises a single linear body that is extended along the transporting direction and winds spirally around a starting point roller and an ending point roller; and
    wherein the conveyor belt is hydrophilic.

4. A thin-section conveyor apparatus as claimed in claim 1, wherein the plurality of longitudinal linear bodies and the plurality of transverse linear bodies are hydrophilic.

5. A method for transporting thin sections using the thin-section conveyor apparatus as claimed in claim 1, comprising:
    transporting the thin sections to a liquid bath with forward rotation of the conveyor belt and setting the thin sections floating on the surface of the liquid bath;
    after a first predetermined time, reverse-rotating the conveyor belt to scoop the thin sections from the liquid bath and mount on the conveyor belt; and
    after a second predetermined time, transporting the thin sections back to the liquid bath with forward rotation of the conveyor belt and setting the thin sections floating on the surface of the liquid bath.

6. A method for transporting thin sections using the thin-section conveyor apparatus as claimed in claim 1, comprising:
    transporting the thin sections to a liquid bath with forward rotation of the conveyor belt and setting the thin sections floating on the surface of the liquid bath;
    after a first predetermined time, scooping the thin sections that are set afloat on the surface of the liquid, by using a thin-section scooping tool,
    wherein the thin-section scooping tool comprises:
        a frame having a pair of filament supporting parts disposed opposite to each other and
        plural linear bodies provided between a pair of linear body supporting parts and disposed in parallel with each other with intervals between each linear body; and
    after a second predetermined time, pushing downward the thin-section scooping tool and setting afloat the thin sections back on the surface of the liquid bath.

* * * * *